United States Patent [19]

Takata et al.

[11] Patent Number: 4,900,801

[45] Date of Patent: Feb. 13, 1990

[54] EPOXY COMPOUNDS AND EPOXY RESIN COMPOSITIONS CONTAINING THE SAME

[75] Inventors: Toshimasa Takata; Hideo Nakamura, both of Chiba, Japan

[73] Assignee: Mitsui Petrochemical Industries, Ltd., Tokyo, Japan

[21] Appl. No.: 199,713

[22] Filed: May 27, 1988

[30] Foreign Application Priority Data

May 29, 1987 [JP] Japan .................................. 62-134393

[51] Int. Cl.$^4$ ............................................. C08G 59/06
[52] U.S. Cl. ........................................ 528/87; 549/560
[58] Field of Search ........................... 528/87; 549/560

[56] References Cited

U.S. PATENT DOCUMENTS

| | | | |
|---|---|---|---|
| 3,057,928 | 10/1962 | Koblitz et al. | 528/87 X |
| 3,336,250 | 8/1967 | Koblitz et al. | 528/87 X |
| 4,072,656 | 2/1978 | Hartmann | 528/87 X |
| 4,677,170 | 6/1987 | Monnier et al. | 528/87 X |

*Primary Examiner*—Earl Nielsen
*Attorney, Agent, or Firm*—Birch, Stewart, Kolasch & Birch

[57] ABSTRACT

A novel epoxy compound having a chemical structure in which an aromatic ring having a glycidyl raedical attached thereto has a tertiary alkyl radical at its ortho or meta-position. An epoxy resin composition comprising the epoxy compound, a curing agent, and a curing accelerator which cures into a product having a low dielectric constant.

12 Claims, 2 Drawing Sheets

EPOXY COMPOUNDS AND EPOXY RESIN COMPOSITIONS CONTAINING THE SAME

BACKGROUND OF THE INVENTION

The present invention relates to epoxy compounds and epoxy resin compositions containing said epoxy compounds as an essential ingredient.

Cured epoxy resins are widely used as electrical insulating materials, adhesives and coating compositions because of improved electrical properties, adhesiveness, and heat resistance. Further improvement in heat resistance, mechanical properties and electrical properties is desired for epoxy resins as severer requirements are imposed in their advanced applications, particularly electric and electronic applications.

Epoxy resins known to form a cured product having higher heat resistance are illustrated as, for example, ortho-cresol novolak epoxy resins (EOCN) and phenolic novolak epoxy resins. However, there still remains a problem that the cured products of these epoxy resins, are brittle.

In addition to the fact that cured epoxy resins are brittle or less flexible, an attempt to improve their heat resistance often results in a further decrease in flexibility. Lack of flexibility gives rise to many problems. For example, a coating composition forms a coating which is susceptible to cracking upon the application of an impact, an adhesive fails to achieve a desired level of peel strength, and a casting composition results in castings which are susceptible to cracking under thermal shock.

Known epoxy resins having improved flexibility are polyalkylene glycol diglycidyl ethers, lactone-modified epoxy resins and the like. Despite improved flexibility, cured articles of these resins are decreased in other properties including heat resistance and mechanical strength. There is a need for epoxy resins having a sufficient degree of heat resistance and flexibility to meet their advanced applications.

In the field of laminated boards, those having a low dielectric constant are desired for the purpose of increasing the compilation speed of computers. Since currently available techniques of fine patterning and densifying to increase the compilation speed have almost reached a physical limit, attention is now paid to another approach to reduce the dielectric constant of board material. Polyethylene and fluoride resins have been proposed as materials having a low dielectric constant. Most of these resins have drawbacks including low mechanical strength, poor dimensional stability, and low copper foil peel strength.

It has also been considered to substitute quartz for glass substrate. An undesirable problem which accompanies the substitution is that a drill used to perforate the substrate becomes severely worn.

There is a requisite for an epoxy resin which is reduced in dielectric constant while maintaining the inherent properties of epoxy resins.

SUMMARY OF THE INVENTION

An object of the present invention is to provide a novel epoxy compound which can form a cured epoxy resin having a lower dielectric constant as compared with conventional epoxy resins while maintaining improved heat resistance and flexibility.

Another object of the present invention is to provide an epoxy resin composition containing such an epoxy compound as an essential ingredient.

According to a first aspect of the present invention, there is provided an epoxy compound having the general formula:

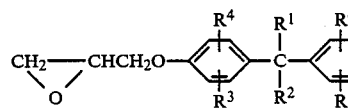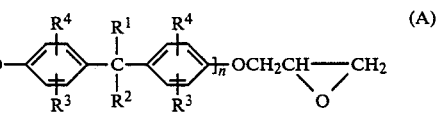 (A)

wherein n is the number of recurring units and has a value in the range of from 0 to 30,
$R^1$, $R^2$, and $R^3$ are independently selected from the group consisting of hydrogen and alkyl radicals having 1 to 6 carbon atoms, and
$R^4$ is a tertiary alkyl radical.

According to a second aspect of the present invention, there is provided an epoxy resin composition comprising
an epoxy compound having the general formula:

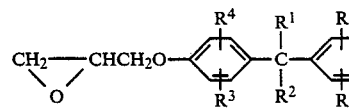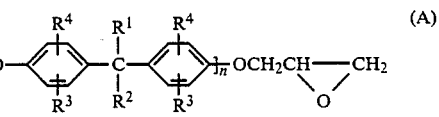 (A)

wherein n is the number of recurring units and has a value in the range of from 0 to 30,
$R^1$, $R^2$, and $R^3$ are independently selected from the group consisting of hydrogen and alkyl radicals having 1 to 6 carbon atoms, and
$R^4$ is a tertiary alkyl radical,
a curing agent, and
a curing accelerator.

DETAILED DESCRIPTION OF THE INVENTION

Figure 1:
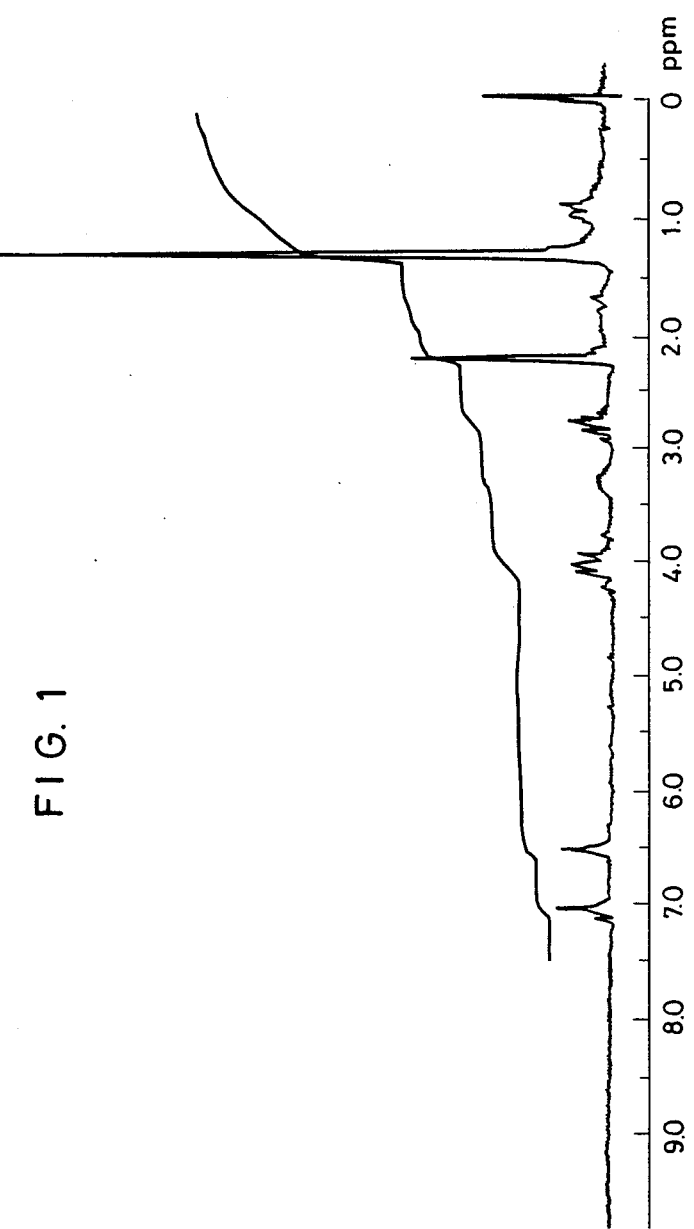
FIGS. 1 and 2 are diagrams showing the $^1$H-NMR and IR spectra of a typical epoxy compound according to the present invention.

The epoxy compound of the present invention is a compound having a novel chemical structure in which an aromatic ring having glycidyl radicals attached thereto has a tertiary alkyl radical such as a tertiary butyl radical preferably at its ortho-position as illustrated by formula (A).

In formula (A), $R^1$, $R^2$, and $R^3$ are independently selected from the group consisting of a hydrogen atom and alkyl radicals having 1 to 6 carbon atoms. Preferably, $R^1$ is a hydrogen or methyl radical, $R^2$ is a methyl or ethyl or propyl radical. Preferably, $R^3$ is a methyl or ethyl radical, especially attached to the aromatic ring at the meta-position with respect to the adjoining oxygen atom. $R^4$ is a tertiary alkyl radical, preferably a tertiary butyl radical, especially attached to the aromatic ring at the ortho-position with respect to the adjoining oxygen atom.

The epoxy resin composition of the present invention contains the above-defined epoxy compound as an essential ingredient and in addition, includes a curing agent and a curing accelerator. The epoxy compound is cured into a low dielectric constant resin which is improved in heat resistance and flexibility as compared with prior art known cured epoxy resins by virtue of steric hindrance incurred by the tertiary alkyl radical of the epoxy compound unit.

The epoxy of compound of formula (A) may be prepared by reacting a bisphenol of general formula (I):

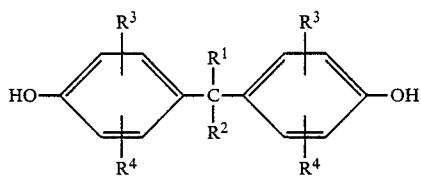

(I)

wherein $R^1$ through $R^4$ are as defined in formula (A), with epichlorohydrin in such a proportion that 3 to 30 mol of epichlorohydrin is present per mol of bisphenol. The preferred examples and position of attachment of substituents $R^1$ through $R^4$ are the same as previously described.

This reaction may be carried out by a variety of prior art methods known for similar types of reaction. One method carries out the reaction of a bisphenol with epichlorohydrin at a temperature of about 60° to about 90° C. in the presence of water by using an alkali compound, for example, an alkali metal hydroxide such as sodium hydroxide, potassium hydroxide and lithium hydroxide, preferably sodium hydroxide in an amount of at least one mol, preferably from 1.02 to 1.05 per equivalent of the phenolic hydroxyl radical of the bisphenol. During the reaction, etherifying and dehydrohalogenation are concurrently effected. At the end of reaction, unreacted halohydrins, water and the resulting salts are removed from the reaction mixture. The epoxy compound reaction product is then dried and recovered.

A method for carrying out etherifying and dehydrohalogenation sequentially rather than concurrently may also be employed, with the advantage of obtaining epoxy resins of consistent quality.

The etherifying step is conducted in the presence of from 0.005 to about 5 mol% of an etherifying catalyst per equivalent of the phenolic hydroxyl radical of the bisphenol. Examples of the etherifying catalyst include tertiary amines such as trimethylamine and triethylamine, tertiary phosphines such as triphenylphosphine and tributylphosphine, quaternary ammonium salts such as tetramethylammonium chloride, tetramethylammonium bromide, tetraethylammonium chloride, tetraethylammonium bromide, and choline chloride, quaternary phosphonium salts such as tetramethylphosphonium bromide, tetramethylphosphonium iodide, and triphenylpropylphosphonium bromide, and tertiary sulfonium salts such as benzyldibutylsulfonium chloride and benzyldimethylsulfonium chloride, with the quaternary ammonium salts being preferred. The etherifying reaction is continued until at least about 50%, preferably at least about 80% of the hydroxyl radical of the bisphenol is etherified. This reaction is generally carried out at a temperature of about 60° to about 110° C. for about 1 to 12 hours. The reaction is preferably carried out in the absence of water although it can take place in the presence of water. If present, water is preferably in a controlled amount of up to about 3.0% by weight of the reaction mixture.

The subsequent dehydrohalogenation step may proceed with the reaction product of the etherifying step per se, that is, without removing unreacted epihalohydrin. The reaction is carried out in the presence of a catalyst which may be an alkaline compound, for example, alkali metal hydroxides, preferably sodium hydroxide as used in the concurrent etherifying/dehydrohalogenation method, in an amount of at least about 0.5 mol, preferably at least about 0.8 mol per equivalent of the phenolic hydroxyl radical of the bisphenol. The amount of an alkali compound used is preferably limited up to 1 mol to avoid such inconvenience as gelation.

The reaction is generally carried out at a temperature of about 60° to 100° C. for about 1 to 3 hours. When the catalyst used is sodium hydroxide, it is preferred to carry out the reaction while removing by-produced water from the reaction system.

The reaction is followed by removal of unreacted epihalohydrin by vacuum stripping, removal of by-produced salts by water washing, and optionally, neutralization with a weak acid such as phosphoric acid and sodium dihydrogen phosphate. The end product, epoxy compound is then dried and recovered.

The novel epoxy compounds of the present invention thus prepared, when used for laminates, preferably have an epoxy equivalent weight (EEW) in the range of from 200 to 2000, preferably from 230 to 1500 and a softening point in the range of from 45° to 130° C., preferably from 55° to 110° C.

One epoxy compound is illustrated below as a typical example of the novel epoxy compounds of the present invention together with its characteristics.

Nomenclature:
1,1-bis(2-methyl-4-hydroxy-5-t-butylphenyl)butane.
Chemical formula:

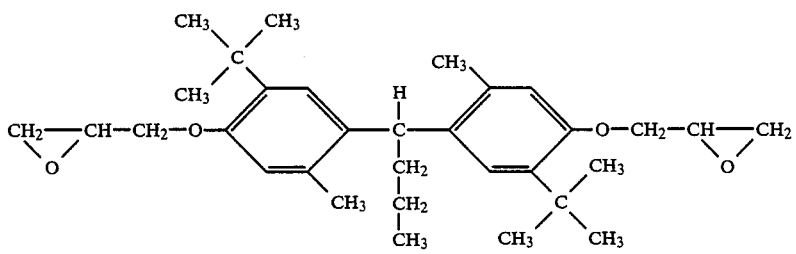

NRM analysis:

FIG. 1 is a diagram of $^1$H-NMR spectrum of the compound.

| δ (ppm) | (TMS standard) | | |
| --- | --- | --- | --- |
| 7.08 | s | 2 | protons |
| 6.53 | s | 2 | protons |
| 3.75–4.25 | m | 4 | protons |
| 3.10–3.50 | m | 2 | protons |
| 2.60–3.0 | m | 4 | protons |
| 2.20 | s | 6 | protons |
| 0.75–2.10 | m | 8 | protons |
| 1.3 | s | 18 | protons |

Figure 2:
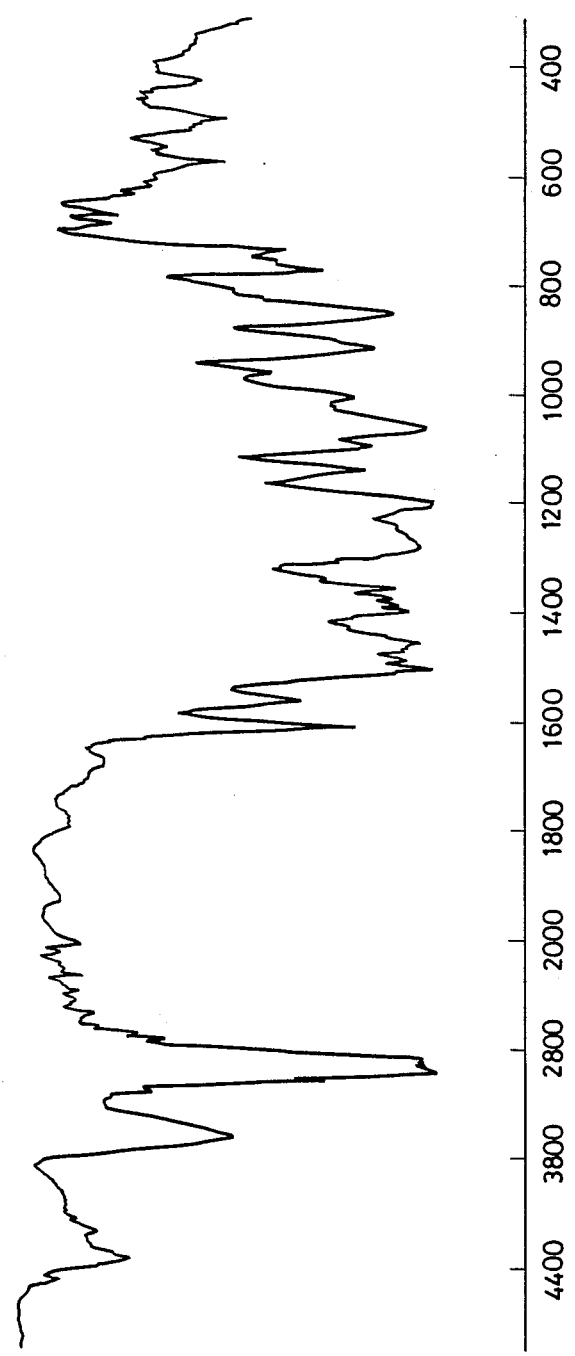

IR analysis:

FIG. 2 is a diagram of IR spectrum of the compound. The compound has a softening point of about 60° C.

The epoxy resin composition of the present invention contains a novel epoxy compound as defined above, a curing agent, and a curing accelerator. The epoxy resin composition may be cured into a product having the following advantages. (1) The cured product has an improved heat resistance because mobility is reduced due to the presence of bulky tertiary alkyl radical represented by $R^4$. (2) The cured product is flexible because it is internally plasticized by the alkyl radicals represented by $R^1$, $R^2$ and $R^3$. (3) The cured product has a low dielectric constant due to the presence of the alkyl radicals, which have many methyl radicals represented by $R^1$ through $R^4$.

The curing agent contained in the epoxy resin composition of the present invention includes acid anhydrides, aromatic polyamines, aliphatic polyamines, imidazoles, and phenol resins, but is not limited thereto.

Examples of the acid anhydrides include phthalic anhydride, hexahydrophthalic anhydride, methyltetrahydrophthalic anhydride, methylhexahydrophthalic anhydride, methylnadic anhydride, pyromellitic anhydride, trimellitic anhydride, benzophenotetracarboxylic anhydride, dodecylsuccinic anhydride, and chlorendic anhydride.

Examples of the aromatic polyamines include diaminodiphenylmethane, diaminodiphenylsulfone, and amine adducts.

Examples of the aliphatic polyamines include triethylenetetramine, diethylenetriamine, menthenediamine, N-aminoethylpiperazine, isophoronediamine, 3,9-bis(3-aminopropyl)-2,4,8,10-tetraspiro[5,5]undecane, and amine adducts.

Examples of the phenol resins include phenolic novolak resins and alkyl-substituted phenolic novolak resins.

Other useful curing agents are dicyandiamide and meta-xylylenediamine.

Examples of the imidazoles include 2-methylimidazole, 2-ethyl-4-methylimidazole, 2-phenylimidazole, 2-undecylimidazole, 2-ethyl-4-methylimidazoleazine, and 1-benzyl-2-methylimidazole.

The curing accelerator contained in the epoxy resin composition of the present invention include imidazoles and tertiary amines as illustrated below.

Examples of the imidazoles include 2-methylimidazole, 2-ethyl-4-methylimidazole, 2-phenylimidazole, 2-undecylimidazole, 2-ethyl-4-methylimidazoleazine, and 1-benzyl-2-methylimidazole.

Examples of the tertiary amines include, N,N-benzyldimethylamine and 2,4,6-tris(dimethylaminomethyl)-phenol.

Other useful curing accelerators are the octylic acid salt of 1,8-diazabicyclo-(5,4,0)undecene-7 which is commercially available under the tradename of Ucat SA 102 from Sun Abot Company, and the complex of monoethylamine and boron trifluoride.

The epoxy resin composition of the present invention may contain another epoxy compound insofar as the other epoxy compound does not adversely affect the composition in accomplishing its objects. The other epoxy compounds used herein are, for example, bisphenol-A epoxy compounds, bisphenol-F epoxy compounds, 1,1-bis(glycidoxyphenyl) ethane, phenolic novolak type epoxy compounds, o-cresolnovolak type epoxy compounds, glycidyl ester type epoxy compounds, glycidyl amine type epoxy compounds, and cycloaliphatic epoxy compounds. When it is desired to impart flame retardancy to the cured epoxy resin composition of the present invention, tetrabromobisphenol-A diglycidyl ether or similar flame retardants may be used in combination.

The epoxy resin composition of the present invention becomes more heat resistant when a phenolic novolak epoxy resin, especially ortho-cresol-novolak epoxy resin is combined with the present epoxy resin in an amount of 0 to 30 parts by weight, preferably 0 to 20 parts by weight per 100 parts by weight of the epoxy resin.

The epoxy resin composition of the present invention may contain a suitable amount of any additive agents in addition to the above-mentioned ingredients, for example, non-reactive diluents such as phthalic esters, glycol ethers and esters, and phenols; reactive diluents such as long chain alkylene oxides, butyl glycidyl ether, phenyl glycidyl ether, and p-butylphenyl glycidyl ether; fillers such as calcium carbonate, clay, asbestos, silica, mica, ground quartz, aluminum powder, graphite, titanium oxide, alumina, iron oxide, glass powder, glass fibers; and coloring agents such as carbon black, Toluidine Red, Hansa Yellow, phthalocyanine Blue, and phthalocyanine Green.

The epoxy resin compositions of the present invention preferably contain the ingredients in such proportion that there are present from about 1 to 150 parts by weight, more preferably from about 3 to 110 parts by weight of the curing agent and from about 0.1 to 3 parts by weight of the curing accelerator per 100 parts by weight of the epoxy resin. The curing agent may be used in a smaller amount when it is dicyandiamide.

The epoxy resin compositions of the present invention are prepared by mixing the ingredients by heating to melt them or by dissolving them in a solvent.

The epoxy resin compositions of the present invention may be cured at room temperature or by heating them at a temperature of from about 60° to 250° C.

EXAMPLES

Examples of the present invention are given below by way of illustration and not by way of limitation.

EXAMPLE 1

A reactor equipped with a stirrer, a reflux condenser, a dropping funnel, and a thermometer was charged with 393.8 grams of 1,1-bis(2-methyl-4-hydroxy-5-tert.-butylphenyl)butane, 1221 grams of epichlorohydrin, and 33 grams of water before the contents were heated to 70° C. When 1,1-bis(2-methyl-4-hydroxy-5-tert.-butylphenyl)butane was dissolved, 1.2 grams of an aqueous solution containing 53.2% by weight of tetramethylammonium chloride was added to the solution, which was stirred for 2 hours at 70° C. Then under vacuum, 169.6 grams of an aqueous solution containing 48% by weight of sodium hydroxide was added at a temperature of 70° C. over 2 hours. During the period of 2 hours, 36.6 grams of water was removed from the reaction system by azeotropic distillation of epichlorohydrin. The distilled epichlorohydrin was separated from water and fed back to the reaction system. The degree of vacuum of the reaction system was controlled such that the amount of water removed from the system per unit time was equal to the sum of the amount of water in the sodium hydroxide solution being added to the system and the amount of water formed by reaction.

After the amount of the sodium hydroxide solution has been added, the reaction mixuture was stirred for a further ½ hour at the temperature. The first ringclosing reaction was completed in this way.

Then, unreacted epichlorohydrin and water were distilled out under vacuum. To the residue were added 634.6 grams of methyl isobutyl ketone and 377 grams of water. The mixture was stirred at 95° C., allowed to stand, and separated into organic and aqueous phases. A sample was taken out of the organic phase and analyzed after solvent removal to find a hydrolyzable chlorine concentration of 0.58% by weight.

The organic phase was added to the reactor and heated to 90° C. before 9.8 grams of an aqueous solution containing 48% by weight of sodium hydroxide, which was 1.5 times the hydrolyzable chlorine content on a molar basis, was added. The reaction mixture was stirred at 90° C. for 2 hours to carry out the second ring-closing reaction. At the end of reaction, 70.4 grams of an aqueous solution containing 30% by weight of monosodium phosphate was added to neutralize the reaction solution, from which an organic phase was separated.

From the organic phase, water was azeotroped off and the inorganic salt was removed by filtration through a glass filter. Methyl isobutyl ketone was distilled off from the filtrate under vacuum, obtaining 485 grams of a vitreous glycidyl product. The resulting epoxy compound had a softening point of 60° C., an epoxy equivalent weight of 307 g/equivalent and a hydrolyzable chlorine concentration of 0.015% by weight. The number of recurring units, n, was equal to 0.27.

EXAMPLE 2

A reactor was charged with 213.8 grams of 1,1-bis(2-methyl-4-hydroxy-5-tert.-butylphenyl)butane, 663 grams of epichlorohydrin, and 21 grams of water before the contents were heated. After the reaction system became homogeneous, 1.2 grams of an aqueous solution containing 53.2% of tetramethylammonium chloride was added. Stirring was continued for 6 hours at 70° C., and then for 2 hours at 80° C.

The subsequent procedure was the same as in Example 1 except that the reaction mixture had a hydrolyzable chlorine concentration of 0.61% by weight before the second ring-closing reaction was initiated.

There was obtained 247 grams of a vitreous glycidyl product, epoxy compound, which had an epoxy equivalent weight of 300 g/equivalent and a hydrolyzable chlorine concentration of 0.007% by weight. The number of recurring units, n, was equal to 0.24.

EXAMPLE 3

An epoxy resin composition was prepared by blending 100 parts by weight of the epoxy compound obtained in Example 1, 55 parts by weight of methylhexahydrophthalic anhydride curing agent (Liqacid MH-700 by Shin-Nihon Rika K.K.), and 0.5 parts by weight of 1,8-diazabicyclo(5,4,0)undecene-7 octylate curing accelerator (Ucat SA 102 by Sun Abot Company) while heating them. The composition was cast into a casting mold and cured for 1 hour at 100° C., 2 hours at 120° C, 2 hours at 150° C., and further 4 hours at 170° C., obtaining a cured epoxy resin.

The cured epoxy resin had the physical properties shown in Table 1.

COMPARATIVE EXAMPLES 1 & 2

Cured epoxy resins were obtained by the same procedure as in Example 3 except that the epoxy compound of Example 1 was replaced by a bisphenol-A epoxy resin having an epoxy equivalent weight of 189 in Comparative Example 1 and an ortho-cresol novolak epoxy resin having an epoxy equivalent weight of 209 (EOCN 103S manufactured by Nihon Kayaku K.K.) in Comparative Example 2, and the epoxy compound was blended with the methylhexahydrophthalic anhydride curing agent and 1,8-diazabicyclo-(5,4,0)undecene-7 octylate accelerator in the proportion shown in Table 1.

The physical properties of the cured epoxy resins are shown in Table 1.

TABLE 1

|  | E3 | CE1 | CE2 |
|---|---|---|---|
| Composition, parts by weight | | | |
| Epoxy compound Example 1 | 100 | — | — |
| Comparative Example 1 | — | 100 | — |
| Comparative Example 2 | — | — | 100 |
| Curing agent | 55 | 86 | 75 |
| Curing accelerator | 0.5 | 0.5 | 0.5 |
| Cured physical properties | | | |
| Glass transition temperature*[1] (°C.) | 178 | 156 | 186 |
| Flexural strength*[2] (kg-f/mm$^2$) | 12.8 | 13.0 | 12.8 |
| Flexural modulus*[2] (kg-f/mm$^2$) | 260 | 290 | 340 |
| Dielectric constant*[2] at 1 kHz | 2.9 | 3.3 | 3.4 |

TABLE 1-continued

|  | E3 | CE1 | CE2 |
|---|---|---|---|
| Dielectric dissipation factor at 1 MHz | 0.0104 | 0.007 | — |

*[1] differential scanning calorimeter
*[2] JIS K 6911

EXAMPLE 4

A homogeneous solution was prepared by blending 29 parts by weight of the resin of Example 1 and 20 parts by weight of p-t-octylphenol novolak having a softening point of 116° C. and an OH equivalent of 214 g/eq and debubbling the mixture at a temperature of −150° C. To the solution was added 0.14 parts by weight of 2-methylimidazole at the temperature. The mixture was further agitated and debubbled before it was cast in a casting mold.

The mixture was cured for 4 hours at 150° C. and further 4 hours at 170° C.

The cured resin showed the following physical properties.

| Glass transition temperature | 150° C. |
|---|---|
| Dielectric constant at 1 MHz | 2.7 |
| Dielectric dissipation factor at 1 MHz | 0.011 |

EXAMPLE 5

A homogeneous solution was prepared by blending 38 parts by weight of the resin of Example 1 and 30 parts by weight of p-nonylphenol novolak having a softening point of 72° C. and an OH equivalent of 250 g/eq and debubbling the mixture at a temperature of 120° C. To the solution was added 0.18 parts by weight of 2-methylimidazole at the temperature. The mixture was further agitated and debubbled before it was cast in a casting mold.

The mixture was cured for 3 hours at 120° C., 2 hours at 150° C. and further 4 hours at 170° C.

The cured resin showed the following physical properties.

| Glass transition temperature | 120° C. |
|---|---|
| Dielectric constant at 1 MHz | 2.8 |
| Dielectric dissipation factor at 1 MHz | 0.008 |

EXAMPLE 6

A varnish composition was prepared by evenly blending 1070 parts by weight of the resin of Example 1, 713 parts by weight of p-t-octylphenol novolak having a softening point of 116° C. and an OH equivalent of 214 g/eq, 10 parts by weight of 2-ethyl-4-methylimidazole, and 560 parts by weight of toluene.

Prepregs were obtained by impregnating glass fabrics (6232/1050/AS450 manufactured by Asahi Shuebell K.K.) with the varnish composition followed by drying.

A laminate was prepared by placing fifteen prepregs prepared above one on another and press molding the stack at 180° C. under a pressure of 10 kg-f/cm² for 60 minutes.

The laminate showed the following properties.

| Resin content (wt %) | 41.1 |
|---|---|
| Glass transition temperature (°C.) | 150° C. |
| Flexural strength (kg-f/mm2) | 51 |
| Flexural modulus (kg-f/mm2) | 1940 |
| Dielectric constant at 1 MHz | 3.4 |
| Dielectric dissipation factor at 1 MHz | 0.0065 |

As is evident from the above data, cured epoxy resins obtained by curing the epoxy resin compositions according to the present invention are heat resistant by virtue of a reduced mobility due to the bulkiness of the tertiary alkyl radical represented by $R^4$ attached to the benzene ring. Despite heat resistance, the cured resins are low in modulus and flexible due to the internal plasticization by alkyl radicals represented by $R^1$, $R^2$, and $R^3$. The cured resins have a low dielectric constant due to the presence of alkyl radicals, mostly methyl radicals represented by $R^1$ through $R^4$.

The novel epoxy compound of the present invention is useful to formulate an epoxy resin composition which when cured, are satisfactorily heat resistant and flexible and has a lower dielectric constant than conventional bisphenol-A epoxy resins and ortho-cresol novolak epoxy resins.

Cured products resulting from the epoxy resin compositions of the present invention are fully heat resistant when used as sealants or insulating coatings in electric and electronic fields and find many uses as useful cured epoxy resins having minimized brittleness and a low dielectric constant.

Obviously, numerous modifications and variations of the present invention are possible in light of the above teachings. It is therefore to be understood that within the scope of the appended claims, the invention may be practiced otherwise than as specifically described herein.

We claim:

1. An epoxy compound having the general formula:

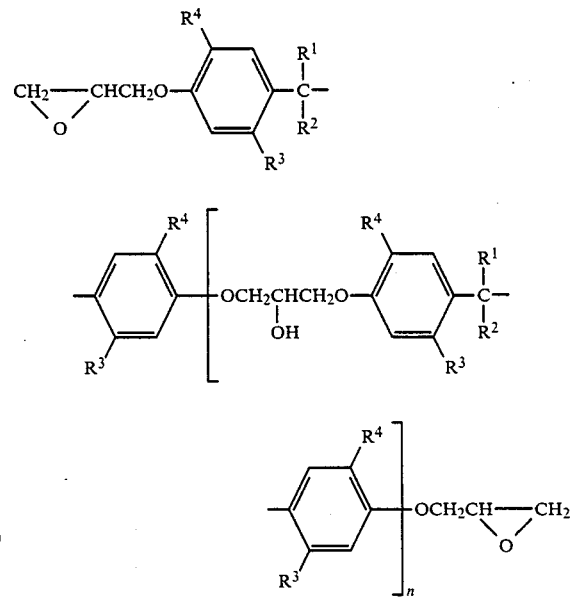

wherein n is the number of recurring units and has a value in the range of from 0 to 30, $R^1$ and $R^2$ are independently selected from the group consisting of hydrogen and an alkyl radical having 1 to 6 carbon atoms, $R^3$ is an alkyl radical having 1 to 6 carbon atoms and
$R^4$ is a tertiary alkyl radical.

2. The epoxy compound according to claim 1, wherein
$R^1$ is hydrogen,
$R^2$ is a methyl radical,
$R^3$ is a methyl radical and
$R^4$ is a tertiary butyl radical.

3. The epoxy compound according to claim 1, wherein
$R^1$ is a methyl radical,
$R^2$ is a methyl radical,
$R^3$ is a methyl radical and
$R^4$ is a tertiary butyl radical.

4. The epoxy compound according to claim 1, wherein
$R^1$ is hydrogen,
$R^2$ is a n-propyl radical,
$R^3$ is a methyl radical and
$R^4$ is a tertiary butyl radical.

5. The epoxy compound according to claim 1, wherein
$R^1$ is hydrogen,
$R^2$ is an ethyl radical,
$R^3$ is a methyl radical and
$R^4$ is a tertiary butyl radical.

6. An epoxy resin composition comprising an epoxy compound having the general formula:

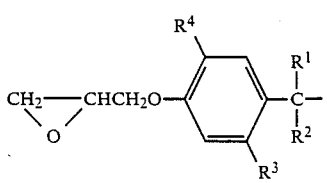

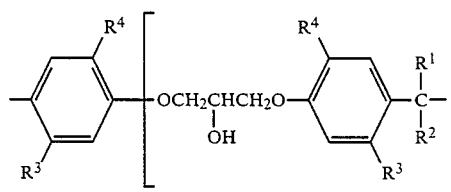

-continued

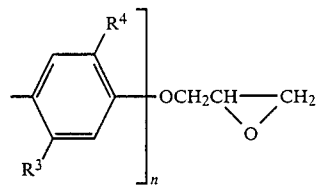

wherein n is the number of recurring units and has a value in the range of from 0 to 30,
$R^1$ and $R^2$ are independently selected from the group consisting of hydrogen and an alkyl radical having 1 to 6 carbon atoms, and
$R^3$ is an alkyl radical having 1 to 6 carbon atoms, and
$R^4$ is a tertiary alkyl radical,
a curing agent and
a curing accelerator.

7. The epoxy resin composition according to claim 6, wherein
$R^1$ is hydrogen,
$R^2$ is a methyl radical,
$R^3$ is a methyl radical and
$R^4$ is a tertiary butyl radical.

8. The epoxy resin composition according to claim 6, wherein
$R^1$ is a methyl radical,
$R^2$ is a methyl radical,
$R^3$ is a methyl radical and
$R^4$ is a tertiary butyl radical.

9. The epoxy resin composition according to claim 6, wherein
$R^1$ is hydrogen,
$R^2$ is a n-propyl radical,
$R^3$ is a methyl radical and
$R^4$ is a tertiary butyl radical.

10. The epoxy resin composition according to claim 6, wherein
$R^1$ is hydrogen,
$R^2$ is an ethyl radical,
$R^3$ is a methyl radical and
$R^4$ is a tertiary butyl radical.

11. The epoxy compound according to claim 1, which has an epoxy equivalent weight in the range of from 200 to 2000 and a softening point in the range of from 45° to 130° C.

12. The epoxy compound according to claim 1, which has an epoxy equivalent weight in the range of from 230 to 1500 and a softening point in the range of from 55° to 110° C.

* * * * *

UNITED STATES PATENT AND TRADEMARK OFFICE
CERTIFICATE OF CORRECTION

PATENT NO. : 4,900,801
DATED : February 13, 1990
INVENTOR(S) : Toshimasa Takata et al.

It is certified that error appears in the above-identified patent and that said Letters Patent is hereby corrected as shown below:

In the patent, at Column 4, line 67, change "1,1-bis(2-methyl-4-hydroxy-5-t-butylphenyl)butane" to -- 1,1-bis(2-methyl-4-glycidyl-5-t-butylphenyl)butane --.

Signed and Sealed this

Twenty-ninth Day of October, 1991

Attest:

*Attesting Officer*

HARRY F. MANBECK, JR.

*Commissioner of Patents and Trademarks*